(12) United States Patent
Wiberg

(10) Patent No.: US 12,702,610 B2
(45) Date of Patent: Aug. 11, 2026

(54) RADIOTHERAPY APPARATUS FOR POSITIONING A SUBJECT

(71) Applicant: Elekta Limited, Crawley (GB)

(72) Inventor: Kristian Wiberg, Crawley (GB)

(73) Assignee: Elekta Limited, Crawley (GB)

( * ) Notice: Subject to any disclaimer, the term of this patent is extended or adjusted under 35 U.S.C. 154(b) by 1002 days.

(21) Appl. No.: 17/906,144

(22) PCT Filed: Mar. 12, 2021

(86) PCT No.: PCT/EP2021/056329
§ 371 (c)(1),
(2) Date: Sep. 12, 2022

(87) PCT Pub. No.: WO2021/180920
PCT Pub. Date: Sep. 16, 2021

(65) Prior Publication Data

US 2023/0111290 A1 Apr. 13, 2023

(30) Foreign Application Priority Data

Mar. 12, 2020 (GB) ...................................... 2003609

(51) Int. Cl.
*A61G 13/00* (2006.01)
*A61G 13/04* (2006.01)
*A61N 5/10* (2006.01)

(52) U.S. Cl.
CPC ................ *A61G 13/04* (2013.01); *A61N 5/10* (2013.01)

(58) Field of Classification Search
CPC ................................ A61G 13/04; A61G 13/02
See application file for complete search history.

(56) References Cited

U.S. PATENT DOCUMENTS 6,640,363 B1 * 11/2003 Pattee .................. A61B 6/0487 5/607
7,373,676 B2 5/2008 Markovic et al.
(Continued)

FOREIGN PATENT DOCUMENTS

GB 2567657 A 4/2019
JP 2016086818 A 5/2016
WO WO-0232312 A1 4/2002

OTHER PUBLICATIONS

"International Application Serial No. PCT/EP2021/056329, International Search Report dated Jun. 17, 2021", (Jun. 17, 2021), 3 pgs.
(Continued)

*Primary Examiner* — Matthew Troutman
*Assistant Examiner* — Ifeolu A Adeboyejo
(74) *Attorney, Agent, or Firm* — Schwegman Lundberg & Woessner, P.A.

(57) ABSTRACT

The present disclosure provides a subject support apparatus for a radiation therapy device comprising a base, a subject support tillable relative to the base, at least two first guides disposed between the subject support and the base and each inclined relative to the base, and a tilting module. The tilting module comprises a first actuator, and a plate disposed between the subject support and the base, and the plate is coupled to an underside of the subject support and to the first actuator such that movement generated by the first actuator is translated into movement of the plate along the at least two first guides, thereby causing the subject support to tilt relative to the base.

19 Claims, 9 Drawing Sheets

(56) References Cited

U.S. PATENT DOCUMENTS

| | | | | |
|---|---|---|---|---|
| 8,215,199 | B2 * | 7/2012 | Marcroft | B25J 17/0216 74/490.13 |
| 8,424,133 | B1 | 4/2013 | Rossi et al. | |
| 11,389,359 | B2 * | 7/2022 | Clayton | A61G 13/04 |
| 2013/0111668 | A1 * | 5/2013 | Wiggers | A61N 5/1049 5/608 |
| 2017/0189719 | A1 * | 7/2017 | Liu | A61G 13/04 |
| 2018/0085603 | A1 | 3/2018 | Kruesi et al. | |
| 2019/0329074 | A1 * | 10/2019 | Wiersma | A61B 34/30 |
| 2020/0405561 | A1 * | 12/2020 | Campagna | A61G 13/1265 |
| 2022/0339469 | A1 * | 10/2022 | Eldered | A61N 5/1081 |
| 2023/0134952 | A1 * | 5/2023 | Carlander | A61G 13/06 5/601 |

OTHER PUBLICATIONS

"International Application Serial No. PCT/EP2021/056329, Written Opinion dated Jun. 17, 2021", (Jun. 17, 2021), 5 pgs.

"United Kingdom Application Serial No. 2003609.1, Examination Report dated Aug. 21, 2020", (Aug. 21, 2020), 5 pgs.

"Chinese Application No. 202180033725.9, Office Action dated Jul. 29, 2025", w English Translation, (Jul. 29, 2025), 11 pgs.

* cited by examiner

RADIOTHERAPY APPARATUS FOR POSITIONING A SUBJECT

PRIORITY APPLICATIONS

This application is a U.S. National Stage Filing under 35 U.S.C. § 371 from International Application No. PCT/EP2021/056329, filed on Mar. 12, 2021, and published as WO2021/180920 on Sep. 16, 2021, which claims the benefit of priority to United Kingdom Application No. 2003609.1, filed on Mar. 12, 2020; the benefit of priority of each of which is hereby claimed herein, and which applications and publication are hereby incorporated herein by reference in their entireties.

The present disclosure relates generally to a radiotherapy apparatus, and in particular to a subject support for a radiotherapy apparatus for positioning a subject during the delivery or application of radiotherapy.

BACKGROUND

In radiotherapy, ionising radiation is used to treat tumours within the human or animal body, by irradiating cells forming part of the tumour with ionising radiation to destroy or damage the tumour cells. However, in order to apply a prescribed dose of ionising radiation to a target location or target region, such as a tumour, the ionising radiation typically also passes through healthy tissue of the human or animal body. As such, while radiotherapy intends to irradiate and damage a predetermined target (e.g. cancerous) region, it can have an undesirable consequence of irradiating and damaging healthy tissues surrounding the target region. Therefore, in radiotherapy treatment, it is desirable to ensure that, while a prescribed dose is delivered to the target region, the dose received by healthy tissues is minimised.

Modern radiotherapy treatment employs techniques to reduce the radiation dose to healthy tissue and thereby provide a safe treatment. For example, one approach to minimising a radiation dose received by healthy tissue surrounding a target region is to direct the radiation towards the target region from a plurality of different angles, for example by rotating a source of radiation around the subject using a rotating gantry. Radiation is emitted in a radiation plane which is co-incident with the plane of the gantry, around which the radiation source rotates to deliver radiation to an isocentre at the centre of the gantry, irrespective of the angular position of the radiation head around the gantry. The angles at which radiation is applied are selected such that each beam of radiation passes through the target region. In this way, a cumulative radiation dose may be built up at the target region over the course of a treatment arc, in which the radiation source rotates through a predetermined angle. Treatments that employ rotation of the gantry in this manner are known as coplanar.

Since the radiation is applied from a plurality of different angles centred on the target region, the specific healthy tissue the radiation passes through varies with the rotation of the radiation head. As such, build up of a high cumulative radiation dose is reduced in the healthy tissue. In other words, each unit volume of the healthy tissue receives a reduced radiation dose relative to a unit volume of the target region.

However, following a 180° rotation of the radiation source, subsequent radiation beams may begin to pass through regions of healthy tissue of a patient previously irradiated, and that this may increase the cumulative radiation dose delivered to these regions of healthy tissue. Moreover, there may be cases where the target region is located behind a healthy organ, and as such it may be difficult or not possible to avoid the healthy organ and deliver the desired radiation dose directly to the target region. It is therefore desirable to enable additional degrees of freedom to reduce the radiation dose delivered to each region of healthy tissue.

One approach to provide an additional degree of freedom so as to spread the radiation dose received by healthy tissue surrounding a target region is to rotate the patient in a plane perpendicular to the plane of radiation as well as rotating the radiation source. Effectively, the angle of radiation varies both in the plane of the gantry and in a plane perpendicular to the gantry about a vertical z-axis. Such an approach is known as non-coplanar.

By rotating the patient in a non-coplanar manner about the vertical z-axis, the radiation dose delivered to each unit volume of healthy tissue in the patient can be further reduced. However, such rotation about the vertical z-axis may result in the target region being shifted away from the isocentre. Further degrees of freedom may therefore be desirable to enable such a shift to be compensated, in addition to enabling further reduction of the radiation dose received by healthy tissues. However, existing systems that are capable of providing one or more further degrees of freedom are expensive and bulky, due to the complex mechanisms required to enable the additional degree(s) of freedom.

In view of the foregoing, it is desirable to provide an improved subject support for a radiotherapy apparatus.

SUMMARY

Aspects and features of the invention are set out in the claims.

According to an aspect of the present disclosure, a subject support apparatus for a radiation therapy device is provided comprising a base, a subject support tiltable relative to the base, at least two first guides disposed between the subject support and the base and each inclined relative to the base, and a tilting module. The tiling module comprises a first actuator, and a plate disposed between the subject support and the base, wherein the plate is coupled to an underside of the subject support and to the first actuator such that movement generated by the first actuator is translated into movement of the plate along the at least two first guides, thereby causing the subject support to tilt relative to the base.

According to another aspect of the present disclosure, a radiation therapy device for delivering radiation to a subject is provided. The radiation therapy device comprises a radiation source configured to emit radiation, and a subject support apparatus comprising a base, a subject support tiltable relative to the base, at least two first guides disposed between the subject support and the base and each inclined relative to the base, and a tilting module. The tiling module comprises a first actuator, and a plate disposed between the subject support and the base, wherein the plate is coupled to an underside of the subject support and to the first actuator such that movement generated by the first actuator is translated into movement of the plate along the at least two first guides, thereby causing the subject support to tilt relative to the base.

Further optional and alternative features of the present disclosure are described in the following exemplary arrangements.

FIGURES

Arrangements of the present disclosure will now be described, by way of example only, with reference to the drawings, in which.

Figure 6A:
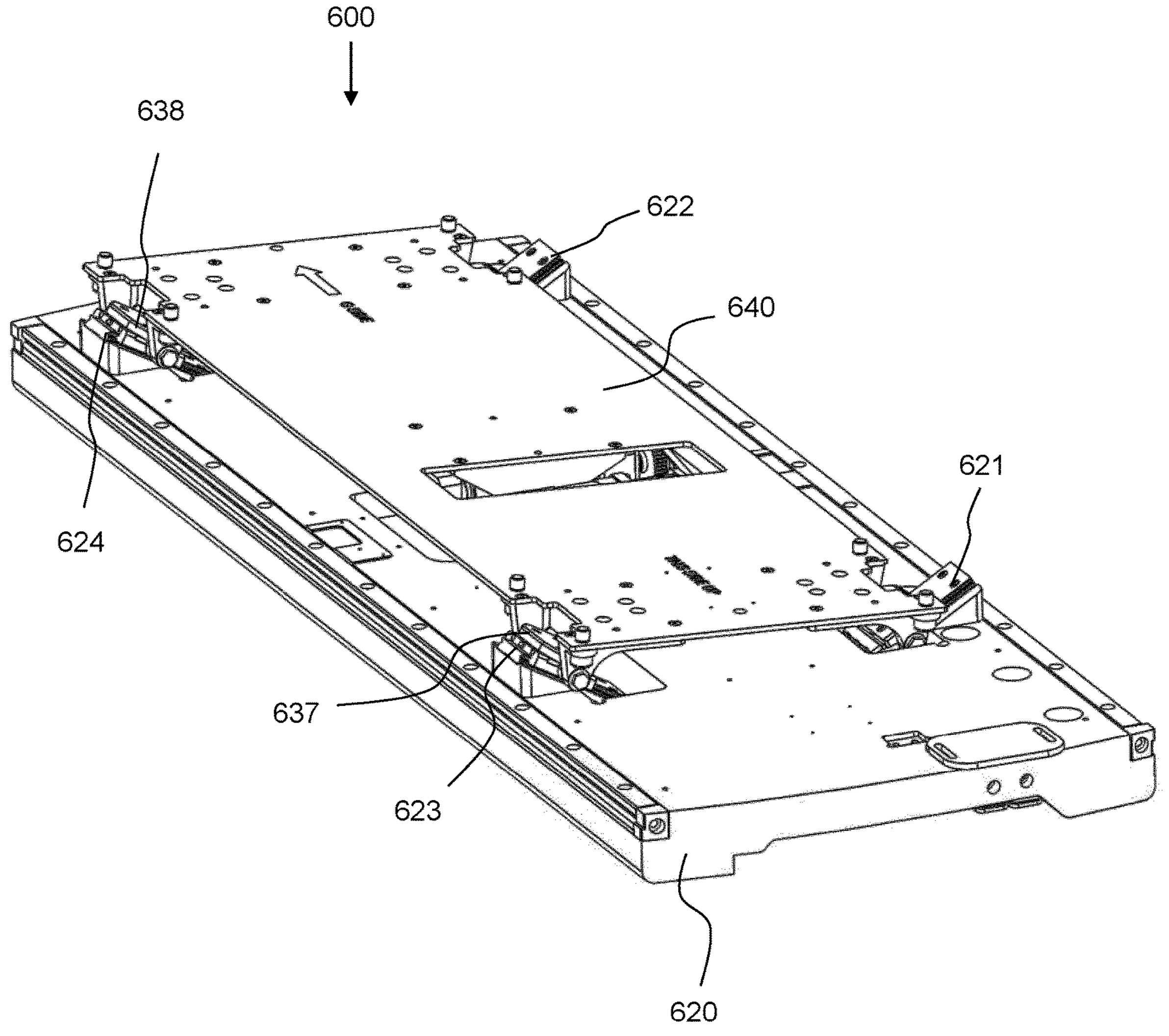

FIG. 6*a* depicts a perspective view of an arrangement of a subject support apparatus.

Figure 6B:
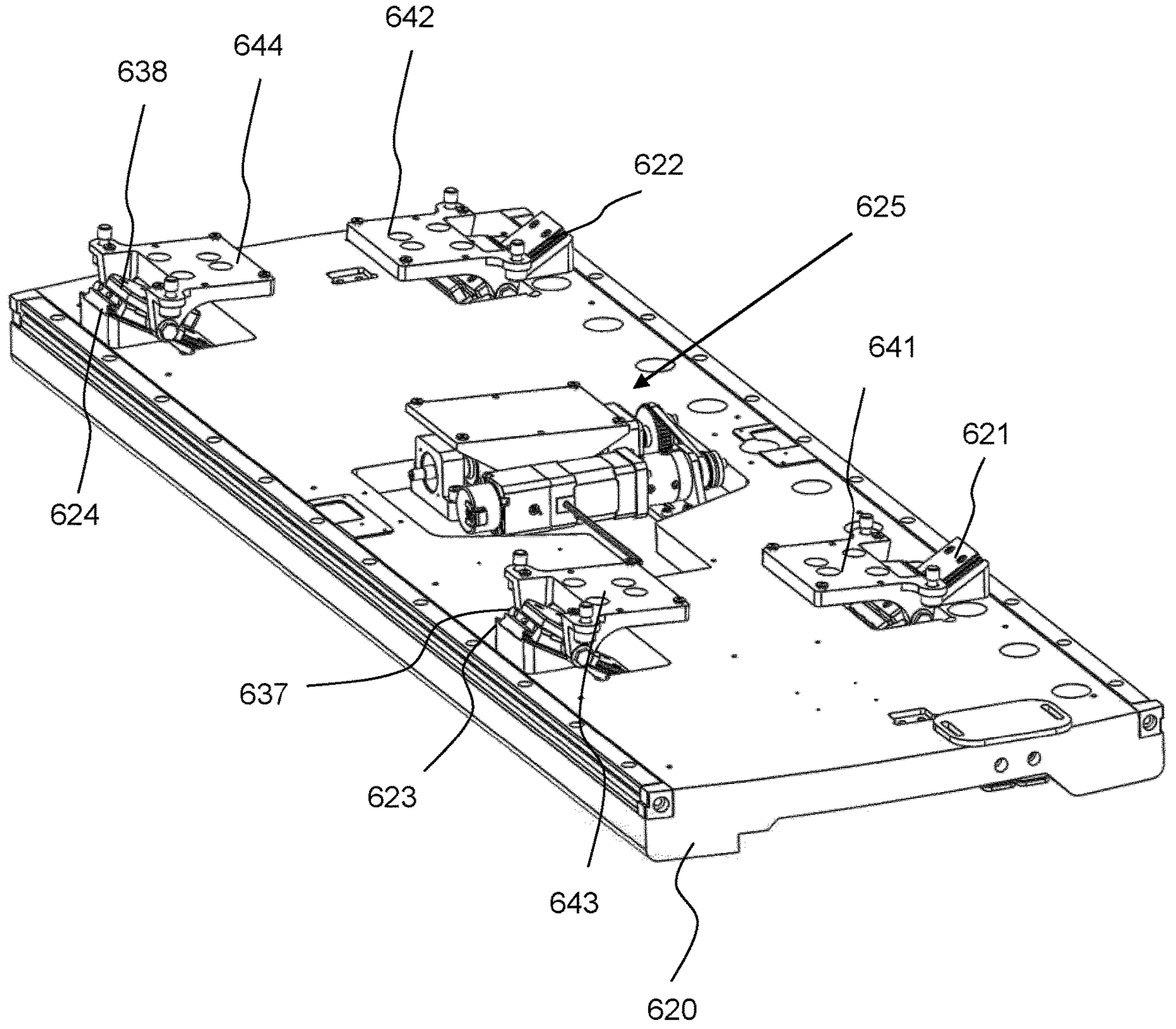
Figure 6C:
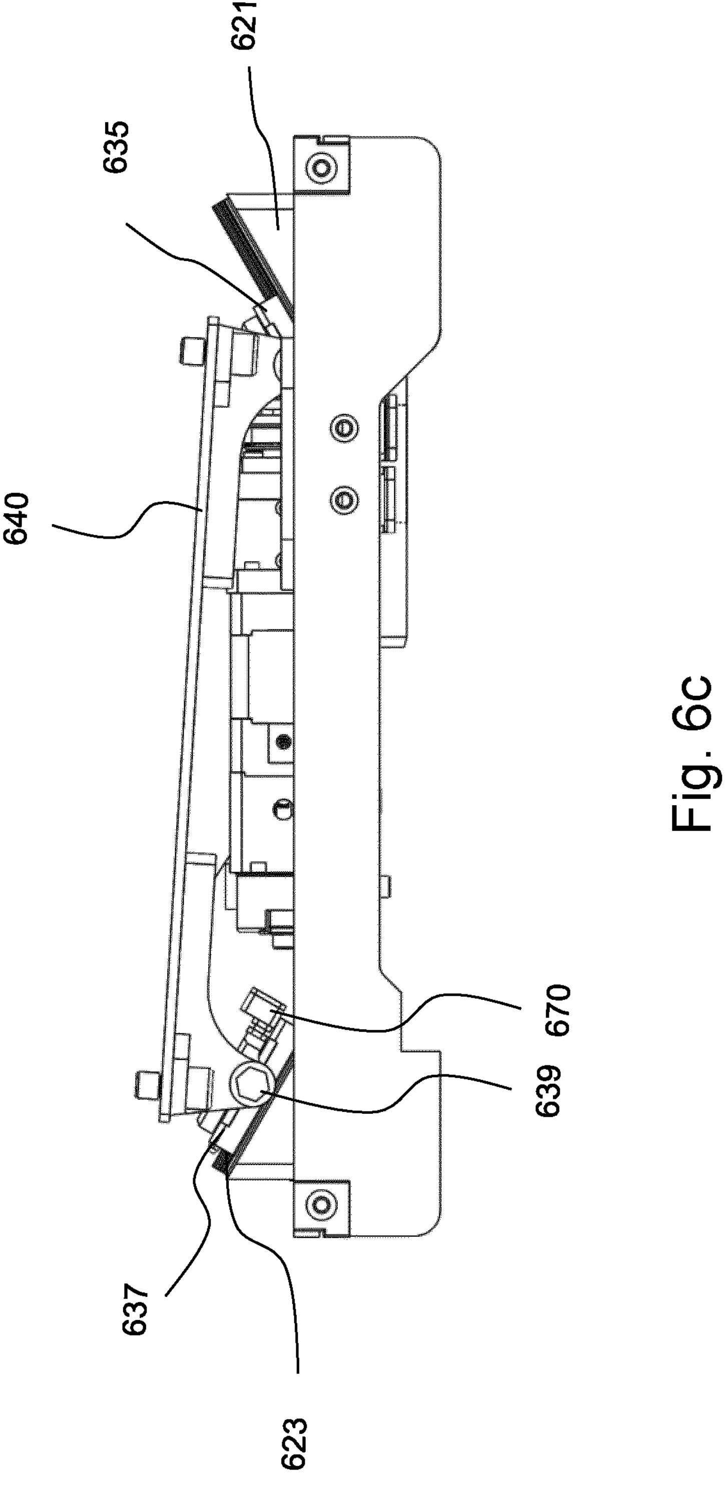

FIG. 6*b* depicts a perspective view of the subject support apparatus of FIG. 6*a* with a plate removed;

FIG. 6*c* depicts a side view from a short side of the subject support apparatus of FIG. 6*a* and FIG. 6*b;*

Figure 7A:
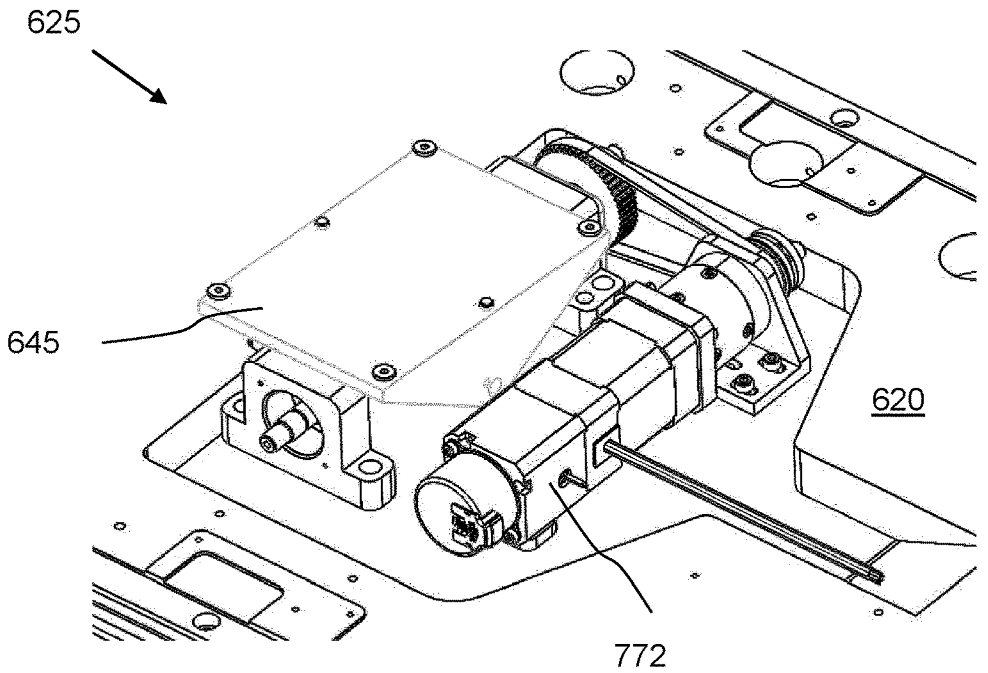
Figure 7B:
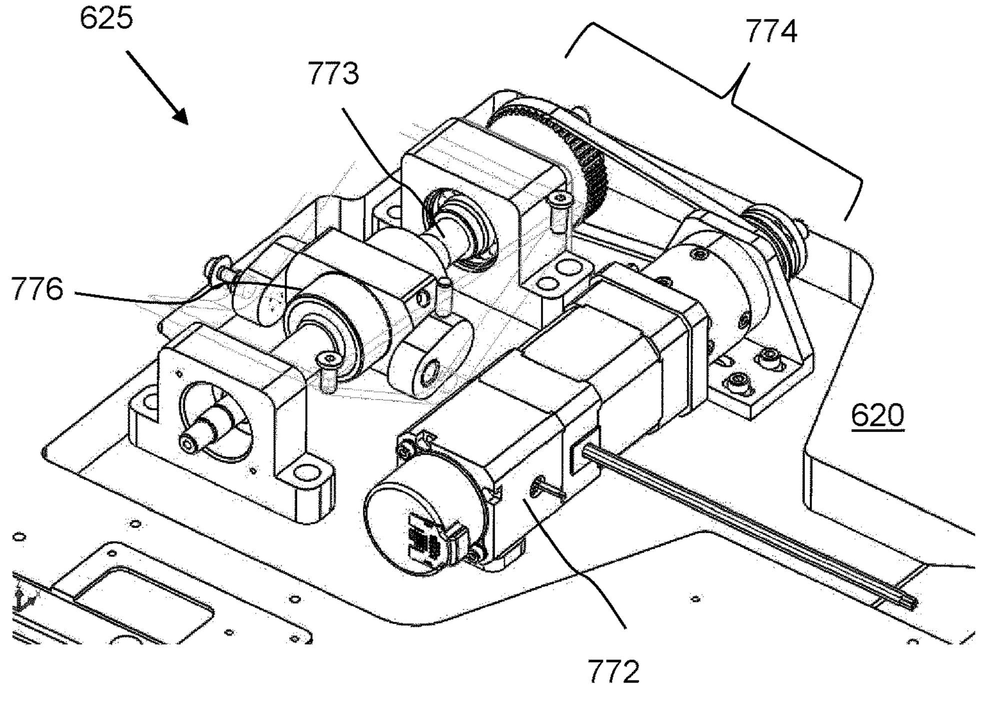

FIG. 7*a* depicts an actuator and a motion converter which may both form part of a tilting module according to the present disclosure;

FIG. 7*b* depicts the actuator of FIG. 7*a* with the movement converter removed so as to better depict the actuator.

DETAILED DESCRIPTION

Arrangements of the present disclosure provides a subject support apparatus for a radiation therapy device. The subject support apparatus may be used for supporting or positioning a subject, such as a human patient or an animal, during radiotherapy treatment. According to preferred arrangements, the subject support apparatus comprises a base, a subject support that is tiltable relative to the base, and at least two first guides and a tilting module that are disposed between the subject support and the base.

In particular disclosed arrangements, the subject support is tiltable relative to the base about a rotation axis, and each of the at least two first guides is inclined relative to the base, with a first subset of the guides on a first side of the base and a second subset of the guides positioned on a second, opposing side of the base, separated by the rotation axis. By positioning inclined guides either side of the rotation axis, such that the guides are each inclined away from the rotation axis, the subject support is naturally biased to a neutral or 'zero' tilt position. Thereby, there is reduced stress or strain on the arrangement which may otherwise be associated with holding the subject support in a zero tilt position.

In particular disclosed arrangements, the first guides extend into recesses formed in the base. Thereby, the gap between the subject support and the base can be advantageously reduced while providing a large maximum angle of tilt.

Figure 3:
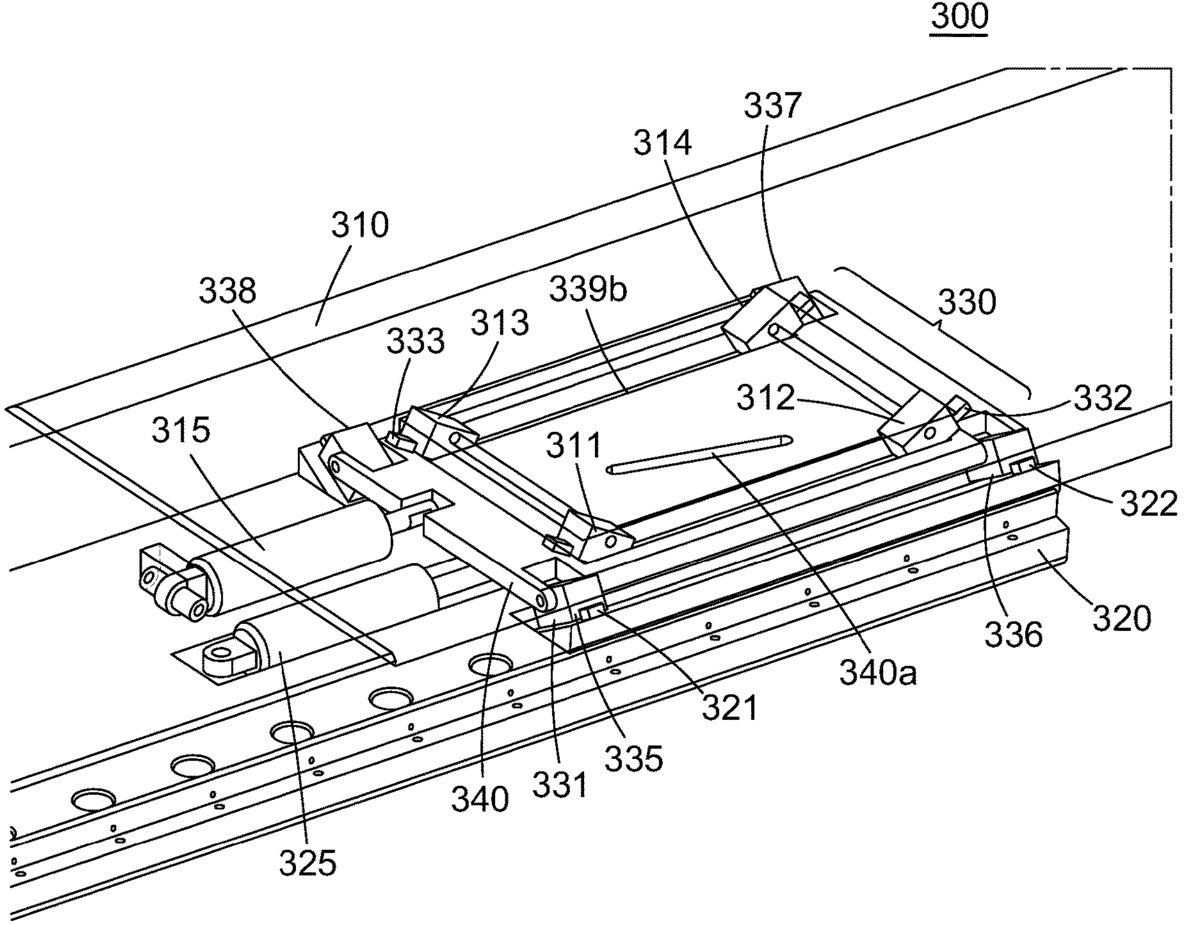
FIG. 3 shows a perspective view of an arrangement of a subject support apparatus.
Figure 4:
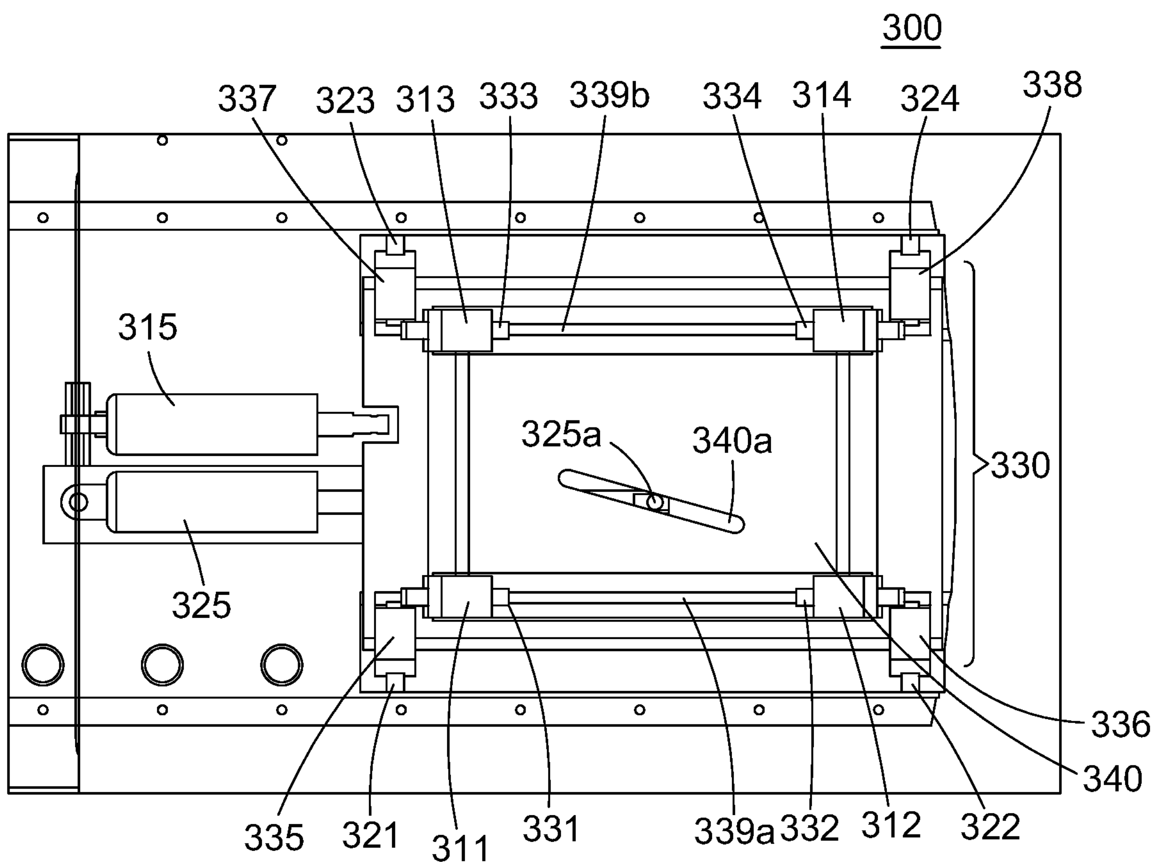
FIG. 4 shows a top view of the subject support apparatus of FIG. 3.

In particular disclosed arrangements, such as the arrangements depicted in FIGS. 3 to 5, the tilting module comprises a first actuator that is operable to generate movement along a second axis substantially perpendicular to the first axis along which the guides are inclined, and the plate is configured to translate movement generated by the first actuator along the second axis into movement of the support surface along the at least two first guides. Thus, an additional degree of freedom is provided to the support surface by tilting the support surface, using a tilting module, about the second axis as it moves along the inclined surface of the at least two first guides. Moreover, by configuring a plate that translates the movement generated by the first actuator in one direction along the second (e.g. longitudinal) axis into movement of the support surface in a perpendicular (e.g. transverse) direction along the inclined surface of the at least two first guides, it is possible to efficiently arrange the tilting module to provide a compact tilting mechanism within a subject support apparatus to enable the tilting motion of the subject support.

In an implementation of the present disclosure, a subject support apparatus for a radiation therapy device comprises a base, a subject support tiltable relative to the base, at least two first guides disposed between the subject support and the base and each inclined relative to the base, and a tilting module. The tilting module comprises a first actuator, and a plate disposed between the subject support and the base, wherein the plate is coupled to an underside of the subject support and to the first actuator such that movement generated by the first actuator is translated into movement of the plate along the at least two first guides, thereby causing the subject support to tilt relative to the base.

In another implementation of the present disclosure, a subject support apparatus for a radiation therapy device comprises a base; a subject support tiltable relative to the base; at least two first guides disposed between the subject support and the base and each inclined relative to the base along a first axis; and a tilting module comprising a first actuator operable to generate movement along a second axis substantially perpendicular to the first axis, and a plate disposed between the subject support and the base, wherein the plate is configured to translate movement generated by the first actuator along the second axis into movement of the subject support along the at least two first guides.

In another implementation, the present disclosure further provides a radiation therapy device for delivering radiation to a subject, comprising a radiation source configured to emit radiation, and a subject support apparatus.

Arrangements of the present disclosure provide an additional degree of freedom to the subject support by tilting the subject support about the second axis as it moves along the inclined surfaces of the at least two first guides. Moreover, by configuring a plate to translate the movement generated by the first actuator in one direction along the second axis into movement of the support surface in a perpendicular direction along the at least two first guides, it is possible to arrange a tilting module that is compact for improved spatial efficiency while enabling the tilting motion of the subject support.

In preferred arrangements, the subject support may be substantially parallel to the base when in a neutral position. This ensures the safety and comfort of the subject (e.g. a human patient) being supported by the subject support when the subject support apparatus is at a starting position.

In preferred arrangements, the at least two first guides may be spaced apart along the first axis proximate to first opposing distal ends of the plate. Such an arrangement provides a wide base for the subject support and allows the weight of the plate and subject support to be more evenly distributed amongst the at least two first guides, thus improving the stability of the subject support.

In preferred arrangements, the at least two first guides may be arranged to incline away from a centre of the plate. In this arrangement, the subject support is biased to move towards a central neutral position, thus improving the stability of the subject support and therefore the safety of the subject (e.g. a human patient) supported by the subject support.

An inclination of each of the at least two first guides relative to the base may be set at any suitable angle. However, in preferred arrangements, the inclination of each of the at least two first guides relative to the base may be in a range between 20 degrees and 40 degrees, preferably 30 degrees.

In preferred arrangements, the plate may comprise an elongated groove along a groove axis at an angle relative to the second axis. In some arrangements, the first actuator may be extendable at a first end in the direction of the second axis, the first end may be arranged within the elongated groove such that extension of the first actuator causes movement of the plate in the direction of the first axis. In this arrangement, extension of the first actuator along the second axis is translated by the elongated groove into movement of the plate along the first axis, causing the plate to slide along the inclined first guides that result in a tilting motion. An arrangement according to the arrangements therefore has an advantage of requiring only simple mechanical elements without the need for complex mechanical designs. As such, costs and time associated with the manufacturing process may be reduced. In some arrangements, the first end of the first actuator comprises a protrusion movably coupled to the elongated groove.

In preferred arrangements, the first actuator may be disposed on the base. In some arrangements, the at least two first guides may be disposed on the base and may comprise a plurality of guide rails, wherein the plate may be coupled to a plurality of corresponding first carriages arranged to slide along the plurality of guide rails. By using conventional or commercially available guide rails and carriages, manufacturing may be further simplified. In some arrangements, the plurality of first carriages may be rotatably coupled to the plate. In such arrangements, the plurality of first carriages may rotate relative to the plane of the plate, such that the plate remains stable as the first carriages slide along the inclined surfaces of the guide rails.

Optionally, the subject support apparatus may further comprise at least two second guides disposed between the subject support and the base each inclined relative to the base along the second axis. The tilting module may further comprise a second actuator operable to generate movement along the second axis, and the plate may be configured to translate movement generated by the second actuator along the second axis into movement of the subject support along the at least two second guides. In this arrangement, the at least two second guides, the second actuator and the plate cooperate to provide a further degree of freedom to the support surface by tilting the support surface about the first axis as it moves along the at least two second guides. In this arrangement, the tilting motion of the support surface about the first axis is separate and independent of the tilting motion about the second axis. As such, it is possible to achieve the desired support surface position and angle with predictable tilting in either or both directions about the first and/or second axis.

Optionally, the at least two second guides may be disposed on the plate and comprise a plurality of guide rails, and the subject support may comprise a plurality of corresponding second carriages arranged to slide along the plurality of guide rails. In some arrangements, the plurality of second carriages may be rotatably coupled to the subject support. In such arrangements, the plurality of second carriages may rotate relative to the plane of the subject support, such that the plate remains stable as the second carriages slide along the inclined surfaces of the guide rails.

Optionally, the at least two second guides may be spaced apart along the second axis proximate to second opposing distal ends of the plate different from the first opposing distal ends, and the at least two second guides may be arranged to incline away from a centre of the plate. The spaced-apart arrangement of the second guides provide a wide base for the support surface, thus improving the stability of the subject support. In some arrangements, an inclination of each of the at least two second guides relative to the base may be in a range between 20 degrees and 40 degrees, preferably at 30 degrees.

In preferred arrangements, the base may have a short side that defines a transverse axis and a long side that defines a longitudinal axis, wherein the first axis may correspond to the transverse axis and the second axis may correspond to the longitudinal axis.

Arrangements of the present disclosure may be implemented to any suitable or desirable radiotherapy device.

Figure 1:
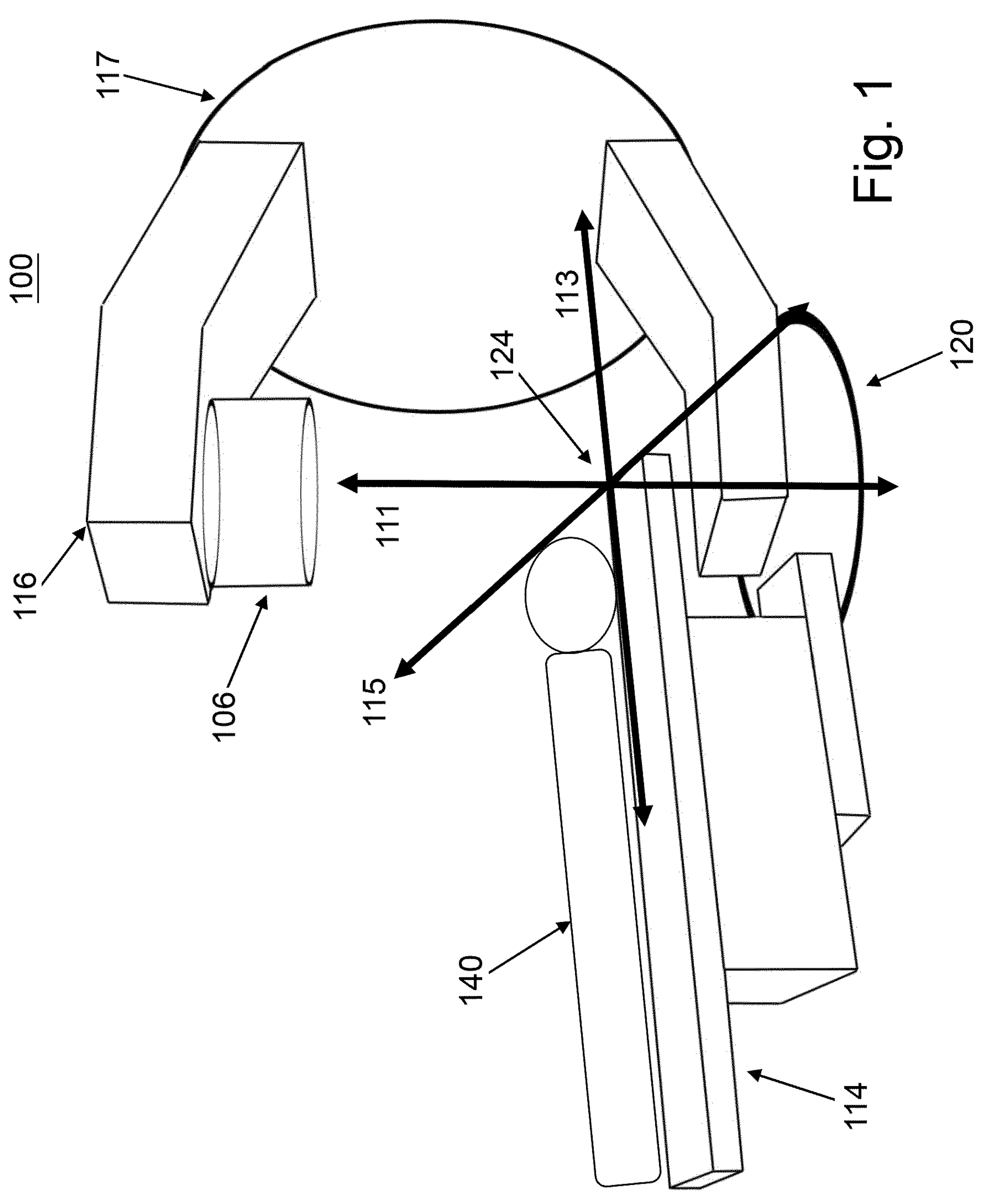
FIG. 1 shows a known radiotherapy apparatus with rotation means located within the plane of the radiation.

For example, arrangements of the present disclosure may be implemented to the radiotherapy device 100 shown in FIG. 1. FIG. 1 shows an example of a non-coplanar radiotherapy device that combines the rotation of the patient with the rotation of the radiation source. A patient 140 is shown supported on a subject support apparatus 114. In the present arrangement, the subject support apparatus 114 is configured to be rotatable around the vertical z-axis 111, while the gantry 116 is configured to be rotatable about the longitudinal y-axis 113 around the subject support apparatus 114. The gantry 116 is a C-arm gantry or open gantry. The rotation mechanism 117 rotates the gantry 116 about the y-axis 113. As the gantry 116 is rotated, radiation is emitted by a radiation source 106 along a radiation axis and around a circle that lies in a radiation plane. Radiation is therefore delivered to the patient 140 from a plurality of angles in the radiation plane.

In the example of FIG. 1, a rotation mechanism 120, disposed under the gantry 116, is provided to rotate the subject support apparatus 114 about an axis of rotation of the subject support apparatus 114 in the radiation plane that coincides with the z-axis 111. In particular, the axis of rotation 111 of the subject support apparatus coincides with the isocenter 124 of the radiotherapy device, such that the subject support apparatus 114 rotates about the isocenter 124. A rotation mechanism 117 is provided for the gantry 116 disposed opposite the subject support apparatus 114 with respect to the axis of rotation 111. In the following discussion, the vertical z-axis 111 is taken to be the axis perpendicular to the plane of the subject support apparatus when it is in its neutral position (parallel to the plane of the floor), the transverse x-axis 115 is taken to be the transverse axis (short side) of the subject support apparatus, and the longitudinal y-axis 113 is taken to be the longitudinal axis (long side) of the subject support apparatus. In the example of FIG. 1, the axis of rotation of the patient support surface 114 coincides with the vertical z-axis 111.

Figure 2:
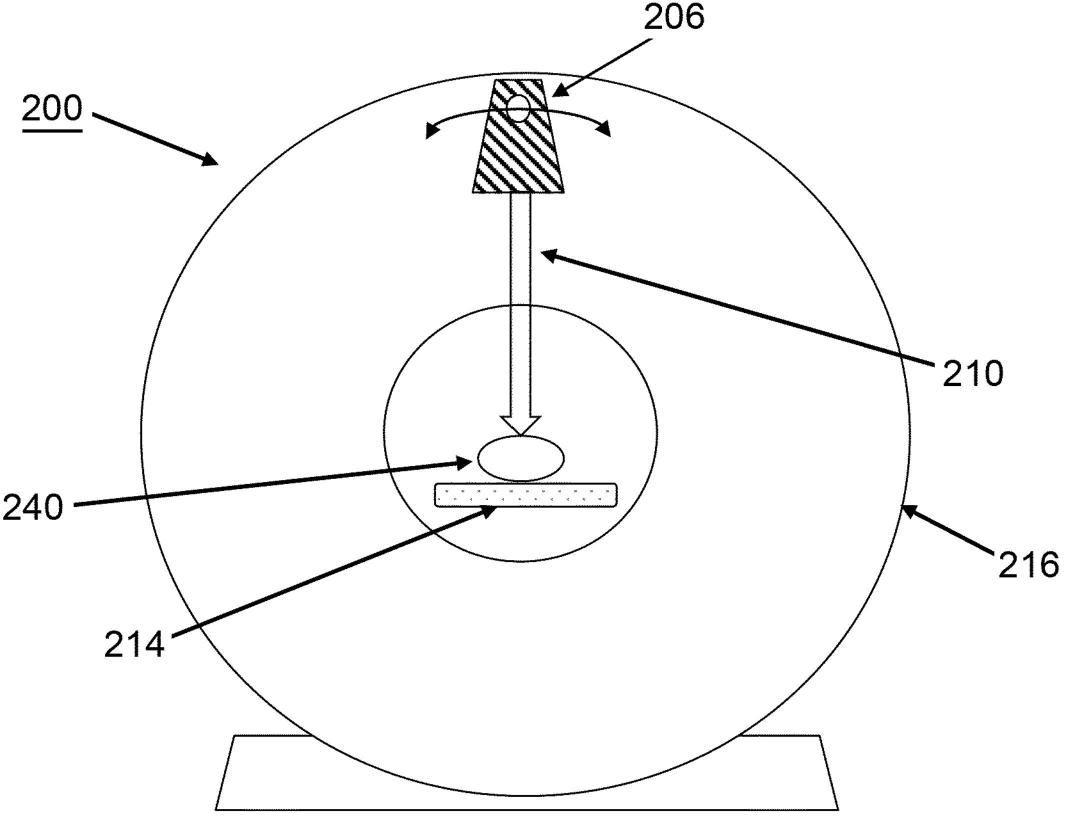
FIG. 2 shows a front view of a radiotherapy device.

FIG. 2 shows another example of a radiotherapy device suitable for implementing arrangements of the present disclosure. In the example, radiotherapy device 200 comprises a ring-based gantry (or bore) 216. The bore of such a radiotherapy device is generally cylindrical, though other shapes may be used as desired. A patient or subject support apparatus 214 is disposed within the bore such that treatment radiation beam 210 from a radiation source 206 is directed towards a patient 240 positioned on the support surface 214. The radiotherapy device 200 comprises a framework, which may otherwise be described as a chassis, a shielding structure, a shell, or a casing. The framework comprises an outer surface which the patient sees upon entering the treatment room, and an inner surface that defines the bore which the patient sees when positioned on the support surface 214. The outer surface and the inner surface of the framework define a hollow region of annular cross-section therebetween in which the gantry 216 rotates. The weight of the ring-based gantry is supported by the floor and thus increasing the device's stability. Moreover, the patient 240 is shielded from the rotatable gantry 216, and operation of the gantry 216 is hidden from the patient's view. This reduces the likelihood of injuries result from the patient or medical staff interfering with the movement of the gantry, and reduces patient's anxiety that may result from the patient directly observing the operation of the gantry. As such, the gantry may be operated to rotate more quickly, efficiently and safely.

FIGS. 3 and 4 show an exemplary subject support apparatus 300 in accordance with an arrangement. The subject support apparatus 300 may be implemented in the subject support apparatus 114 of the radiotherapy device 100 and/or the subject support apparatus 214 of the radiotherapy device 200. The subject support apparatus 300 comprises a subject support 310, a base 320. The subject support 310 may be referred to as a subject support surface. During radiotherapy, a subject (e.g. a human patient) is positioned on, and supported by, the top surface of the subject support 310. The base 320 supports the subject support 310. The subject support 310 and the base 320 define a space therebetween and are parallel with each other when the support surface 310 is in a neutral position.

In the arrangement, the subject support apparatus 300 further comprises first guides 321, 322, 323, 324 disposed on the base 320, a plate 340 with an angled elongated groove or slit 340*a*, a first actuator 325 disposed within a groove in the base 320 with an extendable end having a protrusion 325*a* movably coupled to the elongated groove 340*a* of the plate 340 (see FIG. 4), and first guide blocks 335, 336, 337, 338 disposed at the four corners of the plate 340 configured to slide along the inclined surface of the corresponding first guides 321, 322, 323, 324. Guides 335,338 are positioned proximate a first distal end of the plate 340, and guides 336, 337 are positioned proximate an opposing distal end of the plate. The elongated groove 340*a* is provided in the plate 340 along a groove axis that is at an angle relative to the longitudinal y-axis. In an arrangement, the elongated groove 340*a* is at an angle in the range of 20 degrees to 30 degrees relative to the longitudinal y-axis. The first actuator 325 and the plate 340 may collectively be referred to as a tilting module 330. In the present arrangement, four first guides 321, 322, 323, 324 and four first guide blocks 335, 336, 337, 338 are provided proximate to the four corners of the plate 340. Providing the first guides and first guide blocks proximate to the edge of the plate 340, and in particular proximate to the corners of the plate 340, provides a wide base that gives stability to the structure, and allows the weight of the subject support 310 to be distributed more uniformly compared to supporting and rotating the subject support on a single pivot point. However, more or fewer first guides and corresponding first guide blocks may be used as desired, and they may be disposed at different locations relative to the plate 340 alternatively or in addition to the corners. For example, only two first guides may be provided with one along each of the long side of the plate 340, or six first guides may be provided with four arranged as shown in the arrangement of FIG. 3 and an additional guide along each of the long side of the plate 340. Preferably each of the guides is provided with a corresponding guide block. In preferred arrangements, the angle of inclination between the inclined surface of each of the first guides relative to the base 320 is within a range of 20 degrees to 40 degrees. Preferably the angle of inclination is within a range of 25 degrees to 35 degrees. Most preferably the angle of inclination is at approximately 30 degrees.

In operation, when the first actuator 325 extends, the protrusion 325*a* at the extendable end of the first actuator 325 travels along the elongated groove 340*a*. Since the first actuator 325 is fixed in its position relative to the base 320, as the ball bearing 325*a* moves along the elongated groove 340*a*, the plate 340 is pushed or shifted in the transverse x-direction. In turn, the movement of the plate 340 causes the first guide blocks 335, 336, 337, 338 to slide along the inclined surfaces of the first guides 321, 322, 323, 324. In the present arrangement, as the first guide blocks 335, 336, 337, 338 slide along the corresponding first guides 321, 322, 323, 324 as a result of the plate 340 being moved along the x-axis relative to the base 320, the plate 340 is lifted relative to the base on a side where two guide blocks slide up the corresponding guides and is lowered on the opposite side where two guide blocks slide down the corresponding guides such that the plate 340 is tilted about the longitudinal y-axis relative to the base 330 and no longer parallel to the base 330. In the present arrangement, the first guide blocks 335, 336, 337, 338 are rotatably coupled to the plate 340 is rotatable at each of the long side of the plate 340, such that the sliding of the first guide blocks 335, 336, 337, 338 along the inclined first guides 321, 322, 323, 324 result in a gradual tilt of the plate 340.

In the present arrangement, the subject support 310 is coupled to the plate 340 in such a way that the subject support 310 moves parallel to the plate 340, such that the tilting of the plate 340 causes corresponding tilting in the subject support 310 about the longitudinal y-axis (roll). Effectively, the plate 340 is configured, through the angled elongated groove 340*a*, to translate the movement generated by the first actuator 325 that is along the longitudinal y-axis, into the movement of the subject support 310 along the first guides 321, 322, 323, 324 that are inclined along the transverse x-axis. While the present arrangement shows an arrangement in which the first actuator 325 generates movement in the y-direction that is translated by the plate 340 into movement in the x-direction, alternative arrangement may be used in which the first actuator 325 may be provided to generates movement in the x-direction, e.g. by rotating the first actuator 325 by 90 degrees, that is translated by the plate 340 into movement in the y-direction to cause tilting in the plate, therefore the subject support 310, about the x-axis (pitch). Although in the present arrangement an actuator (first actuator 325) is used to generate linear movement, a different drive unit may be user if desired.

In the present arrangement, the subject support apparatus 300 may optionally further comprise second guides 331, 332, 333, 334 disposed inwards from the four corners of the plate 340, and second guide blocks 311, 312, 313, 314 disposed on the underside of the subject support 310. A second actuator 315 is rotatably coupled to the underside of the subject support 310 at one end and rotatably attached to the plate 340 at an extendable end to enable vertical movement of the subject support 310 allowing it to be lifted or lowered relative to the base 320 by the motion of the second actuator 315. The plate 340 has two cut-out sections 339*a*, 339*b* at opposing sides of the plate 340 along the longitudinal y-axis, which allow the second guide blocks 311, 312, 313, 314 to slide up and down the inclined surface of the second guides 331, 332, 333, 334. In the present arrangement, four second guides 331, 332, 333, 334 and four second guide blocks 311, 312, 313, 314 are provided at the four corners of the plate 340 inward from the first guides and first guide blocks. However, more or fewer second guides and corresponding second guide blocks may be used as desired, and they may be disposed at different locations relative to the plate 340 alternatively or in addition to the corners. In preferred arrangements, the angle of inclination between the inclined surface of each of the second guides relative to the base 320 is within a range of 20 degrees to 40 degrees. Preferably the angle of inclination is within a range of 25 degrees to 35 degrees. Most preferably the angle of inclination is at approximately 30 degrees.

Figure 5A:
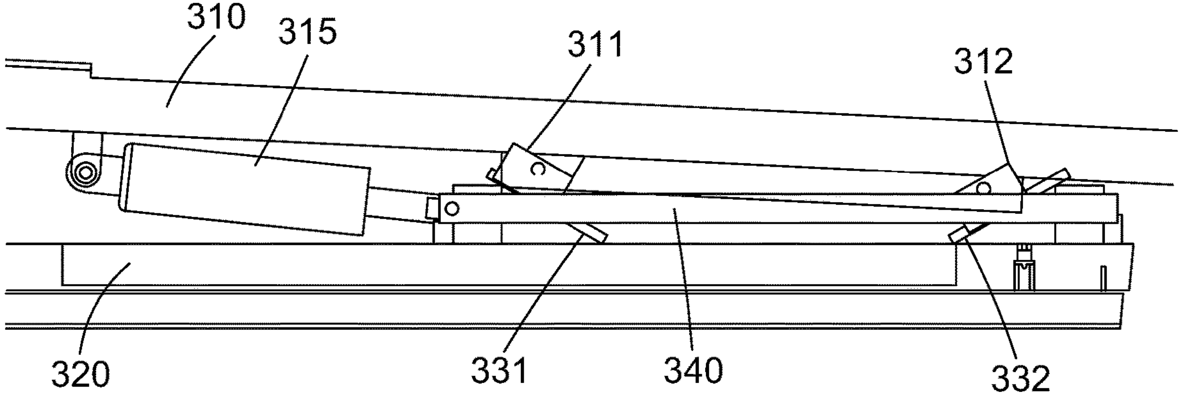
FIG. 5A shows a side view from a long side of the subject support apparatus of FIG. 3.
Figure 5B:
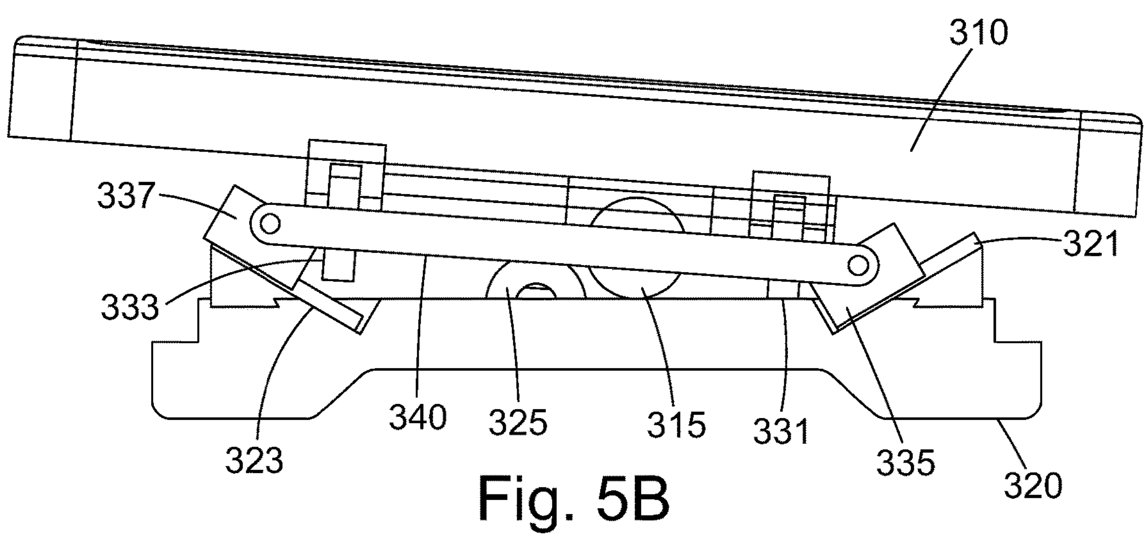
FIG. 5B shows a side view from a short side of the subject support apparatus of FIG. 3.

As can be seen in FIGS. 5A and 5B, in the present arrangement, the first guides 321, 322, 323, 324 are arranged to inclined away from the central longitudinal axis of the base 320, while the second guides 331, 332, 333, 334 are arranged to inclined away from the central transverse axis of the plate 340.

Such arrangement has an advantage of biasing the subject support 310 towards a central neutral position when the subject support 310 is parallel to the base 320 (horizontal). Moreover, providing the first guides, and optionally the second guides, along opposing sides of the plate 340, and preferably proximate to the corners of the plate 340 according to the present arrangement, allows a subject supported by the subject support 310 to remain at the same height with respect to the ground, such that the potential energy of the subject remains unchanged irrespective of the amount of tilting around the x-axis (pitch) and/or the y-axis (roll). In other words, the centre of gravity of the subject remains at the same height from the ground. Since the weight of the subject is not lifted or lowered whether the subject support is pitched or rolled, the amount of energy input required to pitch or roll the subject support is significantly lower, which allows relatively small motors, drive units or actuators to be used, leading to a cheaper more compact subject support apparatus.

In operation, the second actuator 315 extends to push against the plate 340, causing the subject support 310 to move in the longitudinal y-direction, which in turn causes the second guide blocks 311, 312, 313, 314 to move along the inclined surfaces of the second guides 331, 332, 333, 334. As such, the subject support 310 is lifted relative to the base on a side where two guide blocks slide up the corresponding guides and is lowered on the opposite side where two guide blocks slide down the corresponding guides, such that the subject support 310 is tilted about the transverse x-axis relative to the base 330 (pitch). Although in the present arrangement an actuator (second actuator 315) is used to generate linear movement, a different drive unit may be user if desired.

As can be seen in the present arrangement, the configuration of the plate 340 enables the first actuator 325 to be positioned adjacent the second actuator 315, allowing the overall arrangement of the tilting module 330 to be compact. The use of an angled elongated groove 340*a* in the plate 340 represents an example of how the plate 340 may be configured to achieve such translation of movement from one direction to a perpendicular direction; however, other suitable implementations may be possible. In the present arrangement, the plate 340 is configured to translate the movement of the first actuator 325 along the longitudinal y-axis into the movement of the subject support 310 along the transverse x-direction. However, it has been contemplated that the first actuator 325 may alternatively be arranged to generate movement in the transverse x-direction, and the plate 340 may then be configured to translate the movement of the first actuator 325 along the transverse x-axis into the movement of the subject support 310 along the longitudinal y-direction, if desired.

In some arrangements, the operation of the first and second actuators 325, 315 may be controlled by means of a software program executed by a processor. However, the operation of the first and second actuators 325, 315 may be manually controlled if desired.

According to arrangements of the present disclosure, the subject support of the subject support apparatus 114 may be tilted or rotated about the transverse (x-) axis 115 (pitch) and/or tilted or rotated about the longitudinal (y-) axis 113 (roll). Thus, according to the present disclosure, it is possible to position a patient 140 with an additional two degrees of freedom. The additional two degrees of freedom (pitch and roll) may be adjusted independently or in combination, and whilst the couch is in a neutral rotational position (yaw) or when it is in a rotated position. For patient's safety and comfort, the amount of pitch and roll is preferably limited to a predetermined maximum angle.

Arrangements of the present disclosure provides an arrangement using simple mechanical elements to achieve one or more additional degrees of freedom in pitch and/or roll, the movement of which can be controlled straightforwardly due to the independent and predictable movement of the support surface in the transverse or longitudinal directions along the inclined surfaces of the guides. The simplicity of the arrangement allows the size of the couch to be kept relatively compact, enabling its centre of gravity to be kept low. The rotation of the support surface about the transverse and longitudinal axes can be arranged to pivot around the same point at the centre of the plate, and as such any compensations required in the x-, y- or z-direction may be minimised. The disclosed arrangement utilising opposing guides limits or prevents the movement of the plate 340, and therefore the subject support 310, to the direction of the axes of the first, and optionally second, guides. In other words, rotation around the z-axis is restricted, or locked, by the arrangement of the guides according to preferred arrangements. As such, additional stabilizing mechanism is not required to prevent accidental rotation around the z-axis while the support surface 310 is rolled or pitched. The positions of the guides provide a wide base for receiving the weight of the support surface and the subject thereon, thereby improving the stability of the support surface. In some examples, the couch 114 or section thereof may be pitched or rolled about an axis that is spaced apart from the isocenter 124 whilst a different section may be moved to compensate and maintain a portion of the couch 114 substantially at the isocenter 124. In this way, it is possible to maximise the spread of the radiation through the healthy tissue whilst maximising the dose of radiation that is delivered to the target region.

FIGS. 6*a*, 6*b*, and 6*c* depict an arrangement according to the present disclosure. The description above, which describes the example arrangements depicted in FIGS. 3-5, is broadly applicable to the present arrangement except where otherwise noted below, and like features are depicted using like reference numerals where appropriate to facilitate understanding.

FIGS. 6*a*-*c* depict an exemplary subject support apparatus 600, though, to better depict the coupling of plate 640 to base 620, the apparatus 600 is depicted without a subject support. In a fully assembled subject support apparatus 600, the base 620 supports a subject support such that a subject (such as a patient) may be positioned on and supported by the subject support in a manner similar or identical to that described above in relation to FIGS. 3 to 5. FIG. 6*a* is an angled view depicting a subject support apparatus 600 comprising a base 620 coupled to a plate 640. FIG. 6*b* depicts the same angled view of the subject support apparatus 600 but with the plate 640 removed so as to better depict the arrangement of a first actuator 625. FIG. 6*c* depicts a front view of the same subject support apparatus 600 depicted in FIG. 6*a*.

When fully assembled with a subject support coupled to the plate 640, the subject support is tiltable with respect to the base 640. The subject support may be tiltable about a first rotation axis, which may be a substantially fixed rotation axis. The first rotation axis is parallel with and/or may be coincident with the longitudinal centre line of the subject support and/or the longitudinal centre line of the plate 640 and/or the longitudinal centre line of the base 620. The arrangements depicted in FIGS. 6*a*-6*c* are configured to provide a roll rotation of the subject support about the first axis. By providing rotation about a substantially fixed rotation axis which is parallel or co-incident with a centre line of the subject support, the distance between a patient positioned on the subject support and the rotation axis is reduced. This reduces the turning moment felt by the patient and results in a rotation that the patient feels more comfortable with.

When the apparatus 600 is fully assembled, the subject support is coupled to the plate 640 in such a way that the subject support moves parallel to the plate 640, such that the tilting of the plate 640 causes corresponding tilting in the subject support 610 about the first rotation axis. This coupling between plate 640 and subject support is a rigid coupling which may be effected via screwing the plate 640 to the underside of the subject support via brackets 641, 642, 643, 644. Each bracket 641, 642, 643, 644 is rotationally coupled to one of a plurality of guide blocks 635, 636, 637, 638, which may take the form of carriages. The movement of these guide blocks 635, 636, 637, 638, which are rotationally coupled to the plate 640, along the inclined guides 621, 622, 623, 624 which are disposed on the base 620, allows the plate 640, and thereby the subject support, to tilt with respect to the base 620.

In the depicted arrangement, the subject support apparatus 600 further comprises first guides 621, 622, 623, 624 disposed on the base 620. The first guides 621, 622, 623, 624 are inclined with respect to the base 620. The first guides 621, 622, 623, 624 are fixed with respect to the base 620 and extend into recesses in the base 620. By providing inclined guides 621, 622, 623, 624 which extend into recesses in the base, a gap between the base 620 and a subject support surface can be advantageously reduced for a given degree of available tilt. Patients undergoing radiotherapy may be frail and their mobility may be limited, and reducing the 'hop-on' height of a subject support apparatus, i.e. the height of the subject support above the floor when in a neutral tilt position, is advantageous as it allows patients to more easily mount and position themselves on the subject support. Reducing the gap between the base 620 and the subject support is also advantageous for other reasons, for example because it reduces the chances that something may be caught in this gap, for example the fingers of a patient or clinician, as the subject support tilts with respect to the base 620.

As can be appreciated from the figures, the first guides 621, 622, 623, 624 are arranged to incline away from a centre of the plate 640. More specifically, the first guides 621, 622, 623, 624 are arranged to incline away from a centre line of the plate 640. In the arrangement depicted, the first guides 621, 622, 623, 624 incline away from a longitudinal centre line of the plate 640 and from the first rotation axis. A first subset of the first guides, denoted by reference numerals 621 and 622, are positioned on a first side of the base 620, and a second subset of the first guides, denoted by reference numerals 623 and 624, are positioned on an opposing, second side of the base 620. The first and second subset of the first guides are thereby positioned either side of the first rotation axis. The guides 621, 622 of the first subset of guides incline away from the centre of the plate and/or away from the first rotation axis in a first direction, and the guides 623, 624 of the second of guides incline away from the centre of the plate and/or away from the first rotation axis in a second direction, with the first direction being opposite the second direction. Each of the first subset of guides 621, 622 faces a respective one of the second subset of guides 623, 624. Accordingly, the subject support is biased to move towards a central neutral position, thus improving the stability of the subject support and guarding against large and sudden changes in the subject support tilt angle should there be a mechanical failure of any kind.

The apparatus 600 further comprises first guide blocks 635, 636, 637, 638 disposed on the plate 640. In the arrangement depicted in the figures, the first guide blocks 635, 636, 637, 638 are disposed at the four corners of the plate 640. As with the arrangement described with respect to FIGS. 3 to 5, the first guide blocks 635, 636, 637, 638 are configured to slide along the inclined surface of the corresponding first guides 621, 622, 623, 624. The guides 621, 622, 623, 624 may comprise a plurality of guide rails in the manner described above, and the guide blocks 635, 636, 637, 638 may comprise a plurality of corresponding first carriages arranged to slide along the plurality of guide rails. The plurality of first carriages may be rotatably coupled to the plate 640 via a rotational coupling. For example, the rotational coupling 639 depicted in FIG. 6*c* couples plate 640 to a carriage which forms part of guide block 637. These rotational couplings allow the plate 640 to tilt as the carriages move up and down the inclined surfaces of the guide rails.

The guide blocks 635, 636, 637, 638 may each be provided with a mechanical stopper 670, as depicted in FIG. 6*c* which defines a maximum degree of tilt of the subject support via its interaction with a base of a recess into which the first guides 621, 622, 623, 624 extend. The use of such stoppers increases the operational lifetime of the subject support apparatus by reducing wear and tear, and ensures the end point of the tilting movement is well-defined. The mechanical stoppers may also provide a degree of cushioning, such as via a spring or the use of resilient material to form the stopper such that the subject support does not come to an abrupt stop at the extremes of its motion. In this way the stoppers 670 improve the patient experience.

As with other arrangements described herein, the apparatus 600 comprises a tilting module positioned between the base 620 and the subject support which comprises the plate 640 and a first actuator 625. The tiling module may further comprise a motion converter 645 configured to couple the plate 640 and first actuator 625 together. The first actuator 625 can best be inspected in FIGS. 7*a* and 7*b*. The plate 640 is coupled to an underside of the subject support such that the subject support tilts with the plate 640. The plate 640 is also coupled to the first actuator 625 such that movement generated by the first actuator 625 is translated into movement of the plate 640 along the first guides 621, 622, 623, 624, thereby causing the subject support to tilt relative to the base 640.

The first actuator 625 is disposed on the base 620. The first actuator is positioned in a recess of the base 620, again so as to reduce the 'hop-on height', i.e. the gap between base 620 and the support when the apparatus 600 is in a neutral tilt position. The first actuator 625 is a linear actuator and comprises an electric motor 772, a belt and pulley arrangement 774, and a drive screw (or lead screw or ball screw) 776. Driving the electric motor 772 causes the position of the screw 776 to change as it moves along a threaded shaft 773. The threaded shaft 773 is positioned along an axis parallel with the transverse axis of the base 620, and perpendicular to the roll rotation axis. In this way, the first actuator 625 is operable to generate movement substantially parallel to the transverse axis of the base 620. The drive screw 776 of the first actuator 625 is coupled to the motion converter 645 such that movement of the drive screw 776 along the threaded shaft 773 is transferred to the plate 640, and this motion is converted into movement of the guide blocks 635, 636, 637, 638 along inclined guides 621, 622, 623, 624. Thus, the first actuator 625 controls a degree of tilt of the subject support. The skilled person will appreciate that the first actuator 625 may take different forms in order to achieve the functionality described herein, and that rather than the form depicted in FIGS. 7*a*-7*b* the first actuator 625 may take any of a plurality of forms; for example, a simple piston as depicted in FIGS. 3-5.

The plate 640 is coupled to the first actuator 625 via a motion converter 645, which may be referred to as a motion converting unit or a motion converting element. The motion converter 645 may have a triangular prism shape. The motion converter 645 is rotationally coupled to the first actuator 625. The motion converter 645 comprises axles or spindles which are configured to co-operate with apertures or indentations on the first actuator 625 in order to define a rotational coupling between the motion converter 645 and the linear actuator 625. The provision of spindles and corresponding indentations or apertures may be reversed. The motion converter 645 is rigidly coupled to the underside of the plate 640, for example via screws or other attachment means.

In operation, when the first actuator 625 extends, the motion is passed via the motion converter 645 to the plate 640. Motion of the first actuator 625 causes movement of the motion converter 645, which in turn causes a tilting action of the plate 640, which in turn causes the subject support to tilt. In a manner similar to the second actuator 315 described above and depicted in FIG. 5*a*, motion of the first actuator 625 along a movement axis is translated to, i.e. causes, movement of the plate 640 along the inclined first guides 621, 622, 623, 624, thereby causing the subject support to tilt about a first rotation axis relative to the base. In the arrangement depicted in FIGS. 6*a-c*, 7*a* and 7*b*, this rotation axis is substantially perpendicular to the movement axis of the first actuator 625.

By coupling the first actuator 625 to the plate 640, e.g. via the motion converter 645, force is applied directly to the tiltable plate. Because the tiltable plate is coupled directly to the tiltable subject support, an efficient transfer of energy and force is provided from the actuator, to the plate, and to the tiltable subject support. This is advantageous over a design which seeks to instead effect a tilting action by applying a force to a moveable inclined surface underneath the subject support in order to force the subject support upward, thereby causing a tilting action about a pivot point. Such a design would require the pivot point to be anchored between the base and upper surface, and such a design would create unnecessary strains and stresses at the pivot point and thus would be more susceptible to mechanical failure.

The subject support apparatus 600 is depicted in the figures as having an axis of rotation parallel to the longitudinal axis of the subject support. This may be described as a roll rotation in the art. However, it should be appreciated that the same mechanism may be used to provide a pitch rotation via reconfiguration and reorientation of the first guides. The subject support apparatus 600 is depicted in the figures as being tiltable about only one axis of rotation, however it should be appreciated that a plurality of second inclined guides and second guide blocks may be provided, in the manner described herein, so as to allow the subject support of apparatus 600 to tilt about a second axis of rotation.

The plate 340, 640 depicted in the figures is advantageous for several reasons. Optionally, it may comprise an elongated groove or slit, as depicted by groove 340*a* in the figures, which facilitates rotation of the subject support about an axis substantially perpendicular to the directions(s) along which the guides are included, as disclosed above. The plate 640 also allows for ease of manufacture, assembly, and testing. In particular, the actuator(s) of the tilting module may be more effectively serviced and repaired and tested with the subject support removed but the plate still in place. In other words, by connecting everything with the plate, the apparatus can be driven and tested without having to mount the table top. In addition, the plate may also be provided with a detachable panel (not shown in the figures), positioned above the first actuator. The panel is sized and positioned to allow service and repair workers to remove the panel and access the first actuator without having to uncouple the entire plate 640 from the first actuator 625 and brackets 641, 642, 643, 644. The panel is detachable from the plate and may be reattached once service work has been completed. In addition, the detachable panel is transparent to allow such workers to observe the first actuator 625 without removing the panel.

However, it is worth noting that the plate is not essential to the tilting function of the present subject support apparatus. With respect to FIGS. 6*a*-6*c*, it will be appreciated by the skilled person that brackets 641, 642, 643, 644 may be screwed directly to the underside of the subject support. Motion converter 645 may also be coupled directly to the underside of the patient support. In such an arrangement, actuation of the first actuator 625 is coupled to an underside of the subject support such that movement generated by the first actuator is translated into movement of the patient support along the at least two first guides, thereby causing the subject support to tilt relative to the base. Accordingly, the plate is an advantageous but optional feature of the present subject support apparatus.

Disclosed herein is a subject support apparatus for a radiation therapy device comprising: a base; a subject support tiltable relative to the base; at least two first guides disposed between the subject support and the base and each inclined relative to the base; and a tilting module comprising a first actuator, wherein the first actuator is coupled to an underside of the subject support such that movement generated by the first actuator is translated into movement of the patient support along the at least two first guides, thereby causing the subject support to tilt relative to the base.

Disclosed herein is a subject support apparatus for a radiation therapy device comprising: a base; a subject support tiltable relative to the base; at least two first guides disposed between the subject support and the base and each inclined relative to the base along a first axis; and a tilting module comprising a first actuator operable to generate movement along a second axis substantially perpendicular to the first axis, and a plate disposed between the subject support and the base, wherein the plate is configured to translate movement generated by the first actuator along the second axis into movement of the subject support along the at least two first guides.

Optionally, the subject support is substantially parallel to the base when in a neutral position.

Optionally, the at least two first guides are spaced apart along the first axis proximate to first opposing distal ends of the plate.

Optionally, the at least two first guides are arranged to incline away from a centre of the plate.

Optionally, an inclination of each of the at least two first guides relative to the base is 30 degrees.

Optionally, the plate comprises an elongated groove along a groove axis at an angle relative to the second axis.

Optionally, the first actuator is extendable at a first end in the direction of the second axis, the first end being arranged within the elongated groove such that extension of the first actuator causes movement of the plate in the direction of the first axis.

Optionally, the first end of the first actuator comprises a protrusion movably coupled to the elongated groove.

Optionally, the first actuator is disposed on the base.

Optionally, the at least two first guides are disposed on the base and comprise a plurality of guide rails, and wherein the plate comprises a plurality of corresponding first carriages arranged to slide along the plurality of guide rails.

Optionally, the plurality of first carriages are rotatably coupled to the plate.

Optionally, the subject support apparatus may further comprise at least two second guides disposed between the subject support and the base each inclined relative to the base along the second axis.

Optionally, the tilting module further comprises a second actuator operable to generate movement along the second axis, and the plate is configured to translate movement generated by the second actuator along the second axis into movement of the subject support along the at least two second guides.

Optionally, the at least two second guides are disposed on the plate and comprise a plurality of guide rails, and the subject support comprises a plurality of corresponding second carriages arranged to slide along the plurality of guide rails.

Optionally, the plurality of second carriages are rotatably coupled to the subject support.

Optionally, the at least two second guides are spaced apart along the second axis proximate to second opposing distal ends of the plate different from the first opposing distal ends, and the at least two second guides are arranged to incline away from a centre of the plate.

Optionally, an inclination of each of the at least two second guides relative to the base is 30 degrees.

Optionally, the base has a short side that defines a transverse axis and a long side that defines a longitudinal axis, and the first axis corresponds to the transverse axis and the second axis corresponds to the longitudinal axis.

Disclosed herein is a radiation therapy device for delivering radiation to a subject, comprising a radiation source configured to emit radiation, and a subject support apparatus according to any arrangement of subject support apparatus described herein.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A subject support apparatus for a radiation therapy device comprising:

a base;

a subject support tiltable relative to the base, wherein a subject support surface of the subject support and the base are parallel with each other when the subject support is in a neutral position;

at least two first guides disposed on an upper surface of the base between the subject support and the base and each inclined relative to the base, wherein each of the at least two first guides is inclined relative to the base along a first axis of the base; and a tilting assembly comprising:

a first actuator; and a plate disposed between the subject support and the base, wherein the plate is coupled to an underside of the subject support and to the first actuator such that movement generated by the first actuator is translated into movement of the plate along the at least two first guides, thereby causing the subject support to tilt relative to the base, wherein the first actuator is operable to generate movement along a second axis substantially perpendicular to the first axis, wherein the plate comprises an elongated groove along a groove axis at an angle relative to the second axis.

2. The subject support apparatus according to claim 1, wherein the at least two first guides are arranged to incline away from a center line of the plate.

3. The subject support apparatus according to claim 1, wherein the subject support is tiltable relative to the base about a first rotation axis, and the at least two first guides are arranged to incline away from the first rotation axis.

4. The subject support apparatus of claim 1, wherein a first subset of the at least two first guides is positioned on an opposing side of the base from a second subset of the at least two first guides.

5. The subject support apparatus of claim 4, wherein the first subset of the at least two first guides inclines in a first direction, and the second subset of the at least two first guides inclines in a second direction, wherein the first direction is opposite the second direction.

6. The subject support apparatus according to claim 1, wherein each of the at least two first guides extends into a respective recess formed in the base.

7. The subject support apparatus according to claim 1, wherein the first actuator is disposed on the base.

8. The subject support apparatus according to claim 1, wherein the at least two first guides are disposed on the base and comprise a plurality of guide rails, and wherein the plate is rotatably coupled to a plurality of corresponding first carriages arranged to slide along the plurality of guide rails.

9. The subject support apparatus of claim 1, wherein the first actuator is operable to generate movement substantially parallel to the first axis of the base.

10. The subject support apparatus of claim 1, wherein the angle is in a range between twenty degrees and thirty degrees, inclusive.

11. The subject support apparatus according to claim 10, wherein the first actuator is extendable at a first end in a direction of the second axis, the first end being arranged within the elongated groove such that extension of the first actuator causes movement of the plate in a direction of the first axis.

12. The subject support apparatus according to claim 11, wherein the first end of the first actuator comprises a protrusion movably coupled to the elongated groove.

13. The subject support apparatus according to claim 10, further comprising:

at least two second guides disposed between the subject support and the base each inclined relative to the base along the second axis.

14. The subject support apparatus according to claim 13, wherein the tilting assembly further comprises:

a second actuator operable to generate movement along the second axis, wherein the plate is configured to translate movement generated by the second actuator along the second axis into movement of the subject support along the at least two second guides.

15. The subject support apparatus according to claim 13, wherein the at least two second guides are disposed on the plate and comprise a plurality of guide rails, and wherein the subject support comprises a plurality of corresponding second carriages arranged to slide along the plurality of guide rails, and wherein the plurality of corresponding second carriages are rotatably coupled to the subject support.

16. The subject support apparatus according to claim 13, wherein the plate comprises first opposing distal ends and second opposing distal ends, and wherein the at least two second guides are spaced apart along the second axis proximate to the second opposing distal ends of the plate different from the first opposing distal ends, and wherein the at least two second guides are arranged to incline away from a center of the plate.

17. The subject support apparatus of claim 1, wherein the plate is configured to translate movement generated by the first actuator into movement of the subject support along the at least two first guides.

18. The subject support apparatus according to claim 1, wherein the subject support is substantially parallel to the base when in a neutral position.

19. A radiation therapy device for delivering radiation to a subject, the radiation therapy device comprising:

a radiation source configured to emit radiation; and a subject support apparatus comprising:

a base;

a subject support tiltable relative to the base, wherein a subject support surface of the subject support and the base are parallel with each other when the subject support is in a neutral position;

at least two first guides disposed on an upper surface of the base between the subject support and the base and each inclined relative to the base, wherein each of the at least two first guides is inclined relative to the base along a first axis of the base; and a tilting assembly comprising a first actuator, and a plate disposed between the subject support and the base, wherein the plate is coupled to an underside of the subject support and to the first actuator such that movement generated by the first actuator is translated into movement of the plate along the at least two first guides, thereby causing the subject support to tilt relative to the base, wherein the first actuator is operable to generate movement along a second axis substantially perpendicular to the first axis, wherein the plate comprises an elongated groove along a groove axis at an angle relative to the second axis.

* * * * *